United States Patent [19]
Mackool

[11] Patent Number: 5,505,693
[45] Date of Patent: Apr. 9, 1996

[54] METHOD AND APPARATUS FOR REDUCING FRICTION AND HEAT GENERATION BY AN ULTRASONIC DEVICE DURING SURGERY

[76] Inventor: Richard J. Mackool, 31-27 41st St., Astoria, N.Y. 11103

[21] Appl. No.: 400,802

[22] Filed: Mar. 8, 1995

Related U.S. Application Data

[63] Continuation-in-part of Ser. No. 367,455, Dec. 30, 1994, abandoned.

[51] Int. Cl.$^6$ .................................................. A61B 17/20
[52] U.S. Cl. ............................................. 604/22; 606/171
[58] Field of Search ....................... 604/22, 902; 601/2; 128/751, 752, 753; 428/36.9, 36.91; 606/167, 168, 169, 170, 171

[56] References Cited

U.S. PATENT DOCUMENTS

| | | | |
|---|---|---|---|
| 4,634,420 | 1/1987 | Spinosa et al. | 604/22 |
| 4,980,231 | 12/1990 | Baker et al. | 428/36.9 |
| 5,026,393 | 6/1991 | Mackool | 623/6 |
| 5,084,009 | 1/1992 | Mackool | 604/22 |
| 5,209,719 | 5/1993 | Baruch et al. | 604/22 |
| 5,286,256 | 2/1994 | Mackool | 604/22 |
| 5,354,265 | 10/1994 | Mackool | 604/22 |

*Primary Examiner*—George Manuel
*Attorney, Agent, or Firm*—Cobrin, Gittes & Samuel

[57] ABSTRACT

A surgical instrument for removing tissue, such as a cataract, from a patient's body includes a hollow vibrating needle surrounded by one or two hollow infusion sleeves. Methods and apparatus for reducing friction between the surface(s) of the sleeve(s) and the outer surface of the needle and/or surrounding ocular tissue are disclosed. Such friction reduction dramatically reduces the amount of heat generated during surgery, thus reducing the possibility of thermal damage to tissue.

25 Claims, 6 Drawing Sheets

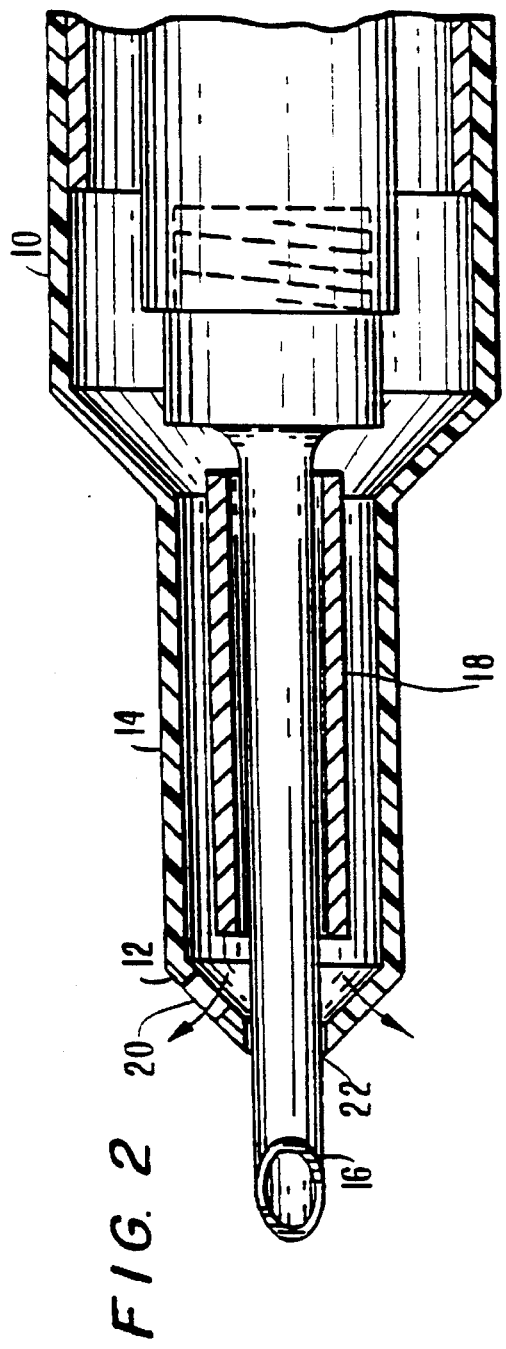
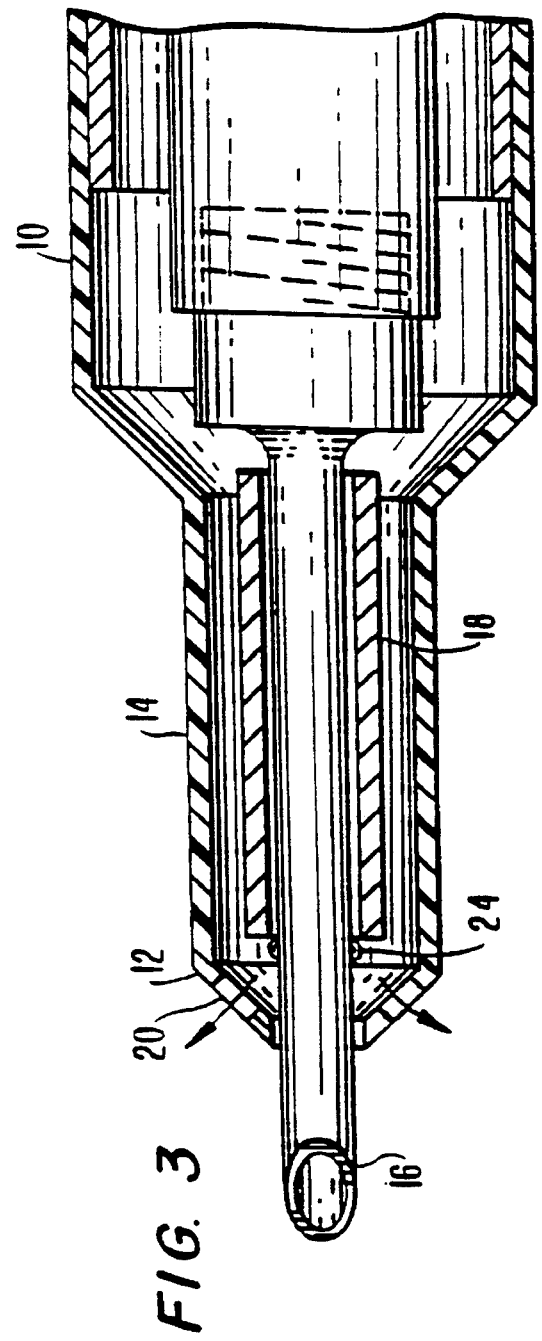

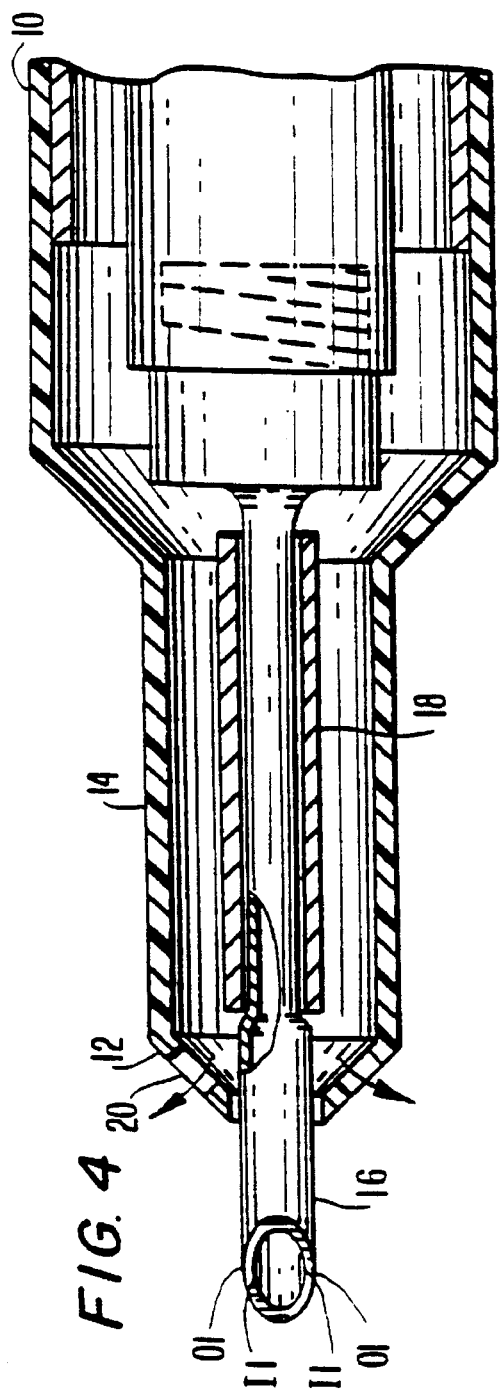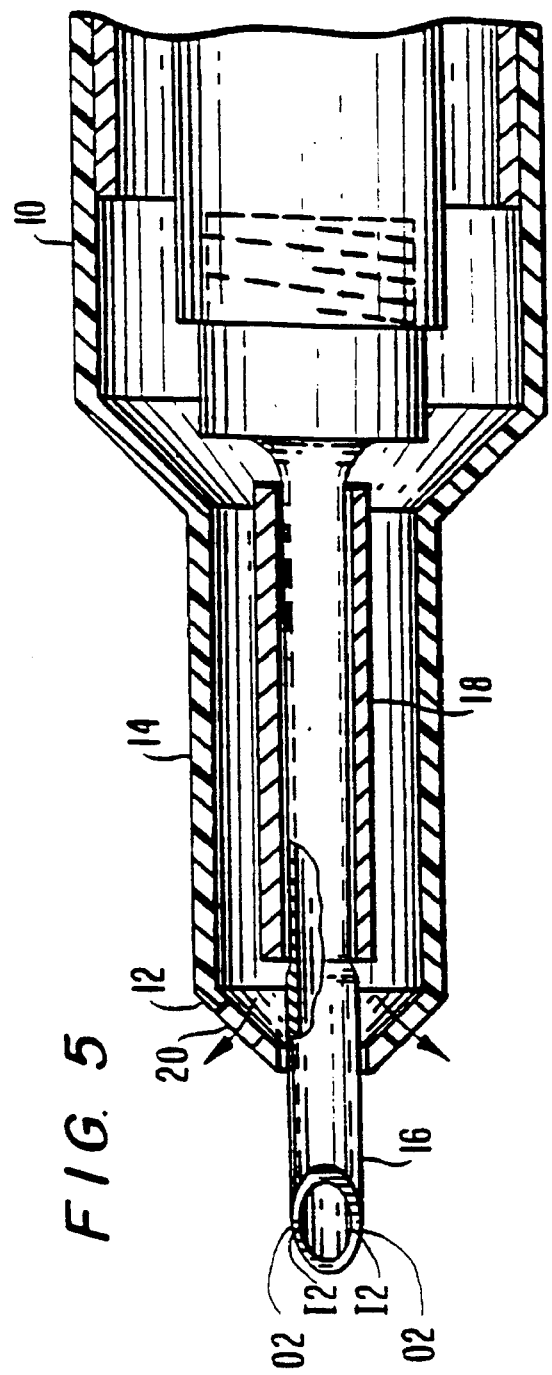

METHOD AND APPARATUS FOR REDUCING FRICTION AND HEAT GENERATION BY AN ULTRASONIC DEVICE DURING SURGERY

CROSS REFERENCE TO RELATED PATENTS

This application is a continuation-in-part of my application, U.S. Ser. No. 08/367,455, filed Dec. 30, 1994 and entitled Improved Method And Apparatus For Reducing Friction And Heat Generation By An Ultrasonic Device During Surgery now abandoned.

FIELD OF THE INVENTION

This invention relates generally to instruments and methods for use in surgery, and, more particularly, to improved ultrasonic instruments and methods which substantially reduce undesirable heat generation during surgery.

The present invention relates to improvements in the methods and apparatus disclosed in U.S. Pat. Nos. 5,084,009, FLUID INFUSION SLEEVE FOR USE DURING EYE SURGERY, 5,286,256, FLUID INFUSION SLEEVE, and 5,354,265, FLUID INFUSION SLEEVE, all by Richard Mackool, the inventor herein, and all incorporated herein by reference.

BACKGROUND OF THE INVENTION

A wide array of fluid-irrigated, ultrasonically-operated cutting devices have been developed for ophthalmological surgical techniques such as phacoemulsification—a method for removing a cataract through a surgical incision in the eye. Examples of such devices are set forth in the following patents:

| Patent No. | Inventor |
| --- | --- |
| 3,589,363 | Banko et al. |
| 4,515,583 | Sorich |
| 4,808,154 | Freeman |
| 4,816,017 | Hood et al. |
| 4,816,018 | Parisi |

U.S. Pat. No. 3,589,363 to Banko et al. and U.S. Pat. No. 4,515,583 to Sorich disclose ultrasonic surgical instruments that utilize rigid outer sleeves.

U.S. Pat. No. 4,808,154 to Freeman discloses a phacoemulsification/irrigation and aspiration sleeve apparatus.

U.S. Pat. No. 4,816,017 to Hood et al. discloses an ultrasonic decoupling sleeve.

U.S. Pat. No. 4,816,018 to Parisi discloses an ultrasonic probe tip.

Fluid-irrigated, ultrasonically-operated cutting devices typical of the prior art, however, suffer from a number of deficiencies. In particular, most infusion sleeves used during phacoemulsification are made of silicone or a silicone-type material. The use of this type of infusion sleeve can cause fluid leakage between the incision edge in the eye and the exterior surface of the infusion sleeve, resulting from a need to make the incision in the eye larger than the infusion sleeve. This need is due to the compressibility of silicone or like materials which cannot be safely used when inserted through an incision in the eye where there is a minimal amount of clearance between the incision and the exterior of the silicone infusion sleeve.

When there is a minimal clearance between the exterior of the silicone infusion sleeve and the incision of the eye, the incision tends to compress the nonrigid silicone infusion sleeve against the vibrating tip which results in relative rubbing movement between the silicone sleeve and the vibrating tip. This relative movement generates undesirable heat as the needle vibrates. The generates of this heat is extremely undesirable inasmuch as it can result in thermal burns and shrinkage of the ocular tissue surrounding the silicone infusion sleeve. The burning and shrinkage of ocular tissue is a serious problem with sight-threatening implications.

In an attempt to reduce the infusion fluid leakage and the deleterious effects that can be caused by undesirable friction generated therefrom, some infusion sleeves have been constructed from rigid, non-compressible materials. Generally these materials have consisted of Teflon or metallic-based compositions. These rigid, infusion sleeves have been relatively successful in solving the problems of constriction of the path for fluid flow between the distal end of the infusion sleeve and the vibrating tip as well as the heat generation and thermal burns associated with malleable infusion sleeves; however, other problems persist with these noncompressible infusion sleeves.

While rigid sleeves are capable of being inserted through smaller incisions, which has the advantage of reducing leakage, there is still significant leakage. The primary cause of the persistent leakage between the rigid infusion sleeve and the eye incision is that the cross section of the rigid sleeve does not match the contour of the eye incision. As a consequence, there are fairly substantial gaps between the rigid sleeve exterior surface and the eye incision. This is because the collagen fiber structure of the cornea resists deformity and thus does not readily assume the shape of the infusion sleeve.

Additionally, vibrating tips have traditionally been made of titanium. While such tips are suitable for the task of vibrating ultrasonically to remove tissue, modification of the tip composition in a way that reduces friction without compromising mechanical integrity would be highly desirable.

The experience of the applicant, who has performed literally thousands of cataract eye operations, has shown that it is impossible, from a practical standpoint, to fully eliminate the problem of leakage during cataract surgery by means of a smaller incision and forcing the rigid infusion sleeve through it. While this may decrease wound leakage, it does not eliminate the problem and it causes the instrument to be so tightly held by the deformed incision that there is great difficulty in advancing and withdrawing the instrument through the incision. As will be apparent to those skilled in the art, during cataract surgery the instrument must be advanced and withdrawn many times through the incision as the fractured portions of the cataract are removed from the various locations within the anterior and posterior chambers of the eye.

In an attempt to prevent heat transmission to ocular tissues, the previously-incorporated Mackool patents teach use of an inner, rigid sleeve, surrounded by an outer, malleable sleeve. While this technique is effective in reducing heat generation, there remains room for improvement. The present invention provides such an improvement. The techniques of the present invention, as described hereinbelow, can be employed by themselves or in combination with any of the methods and apparatus described in the previously-incorporated Mackool patents.

Accordingly, there exists a need for an improved apparatus for performing cataract surgery.

SUMMARY OF THE INVENTION

One object of the present invention is an improved method and apparatus for performing cataract surgery, or like surgical procedures.

Another object of the invention is a method and apparatus for reducing heat generation in cataract eye surgery, or like surgical procedures.

Still another object of the invention is a method and apparatus for reducing heat generation in cataract eye surgery, or like surgical procedures, performed using the methods and apparatus disclosed in the previously-incorporated Mackool patents.

Yet another object of the invention involves use of a thin coating of a rigid, smooth material on friction-inducing surfaces of an ultrasonic surgical instrument. Advantageously, the coating is sufficiently thin that otherwise compliant components remain substantially compliant notwithstanding the additional friction-reducing coating.

Yet another object of the invention involves use of an ultrasonically-vibrating needle whose composition has been altered so as to reduce friction along its surface.

Other general and specific objects of the invention will in part be obvious and will in part appear hereinafter.

In accordance with one aspect of the invention, a surgical instrument for removing a cataract through an incision in a patient's eye illustratively comprises: a hollow, compressible infusion sleeve having a tapered, ported, distal end portion and an extreme end portion; the hollow, compressible infusion sleeve further including a cylindrical portion intersecting with and extending away from the tapered, ported, distal end portion; a hollow, vibrating needle, having an inner needle surface, located at an inner needle diameter, and an outer needle surface, located at an outer needle diameter, and supported by a needle support, the hollow, vibrating, needle extending into a patient's eye during the removal of a cataract; the cylindrical portion and the tapered, ported, distal end portion surrounding the hollow, vibrating needle with there being a space between the extreme end portion of the tapered, ported distal end portion and the hollow, vibrating needle; a rigid, hollow, sleeve surrounding a portion of the hollow, vibrating needle; the sleeve having an outer sleeve surface, located at an outer sleeve diameter, and an inner sleeve surface, located at an inner sleeve diameter; the inner sleeve diameter being larger than the outer needle diameter, thereby defining a path of fluid between the hollow vibrating needle and the rigid, hollow, sleeve; the rigid, hollow, sleeve being surrounded by the cylindrical portion, whereby the rigid, hollow, sleeve prevents the hollow, compressible infusion sleeve from collapsing against the hollow, vibrating needle; an inhibitor for inhibiting the distal migration of the rigid, hollow, sleeve; and, in accordance with the present invention, wherein at least one sleeve surface and/or the outer needle surface is/are adapted to reduce friction between the surfaces and/or between the outer surface of the outer infusion sleeve and the surrounding tissues. The outer needle surface and/or the one or more sleeve surface(s) are preferably adapted to reduce friction by either: (i) adapting either or both surfaces to have a surface energy as close as possible to that of water, thereby ensuring that a thin layer of water remains between the surfaces during operation of the apparatus; or (ii) providing a permanent, nontoxic, biocompatible lubricant, such as graphite or molybdenum sulfide, on the surface(s).

In accordance with another aspect of the invention, a surgical method for removing a cataract through an incision in a patient's eye illustratively includes the steps of: inserting a hollow sleeve into the incision; providing a hollow, vibrating needle through the sleeve; providing a supply of water through the hollow sleeve into the eye; removing the supply of water through the hollow portion of the vibrating needle; and wherein the improvement of the present invention comprises maintaining reduced friction between the outer surface of the vibrating needle and the adjacent inner surface of the hollow sleeve and/or between the outer surface of the sleeve and the surrounding tissue, so as to reduce heat transfer to the patient's eye. Reduced friction is preferably maintained by either: (i) adapting one or more surface(s) to have a surface energy as close as possible to that of water, thereby ensuring that a thin layer of water remains between the surface(s) during the aforesaid steps; or (ii) providing a permanent, nontoxic, biocompatible lubricant, such as graphite or molybdenum sulfide, on one or more of the surface(s).

In accordance with yet another aspect of the invention, an improved ultrasonically-vibrating needle, and an improved surgical procedure using the same, preferably employ an improved needle made from a composite material, such as carbon organic matrix composite or carbon metallic matrix composite. The improved needle is stronger and lighter than traditional designs, and thus can be thinner. This, in turn, provides a sharper cutting edge, which penetrates tissue more readily.

In addition to the above methods, friction is further reduced by making the surfaces of the needle and sleeve(s) which contact each other relatively non-compliant (on a microscopic scale) so that, as these surfaces compress against each other due to compression from the incision, mechanical coupling of microscopic ridges on the surfaces does not occur and transfer of energy to the sleeve(s) is minimized. Such non-compliance can be obtained while still permitting the sleeve(s) to remain grossly deformable, so as to permit conformance to the shape of the incision, and thereby prevent leakage of fluid between the sleeve(s) and the incision. This advantageous combination of (microscopic) non-compliance and (macroscopic) compliance can be achieved in several ways, as described in detail below.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which:

FIG. 2 depicts an embodiment of a phacoemulsification instrument in accordance with the invention; including details of a rigid, hollow sleeve as well as details of the outer deformable sleeve tightly conforming to the vibrating needle at the tapered distal end;

FIG. 3 depicts a second embodiment of a phacoemulsification instrument in accordance with the invention; including details of a rigid, hollow sleeve along with details of a vibrating needle containing protuberances;

FIG. 4 depicts a third embodiment of a phacoemulsification instrument in accordance with the invention; including details of a rigid, hollow sleeve along with details of a tapered vibrating needle, wherein the inner and outer diameters of the vibrating needles are varied along the length thereof;

FIG. 5 depicts a fourth embodiment of a phacoemulsification instrument in accordance with the invention; including details of a rigid, hollow sleeve along with details of a tapered vibrating needle, wherein the inner diameter of the vibrating needle remains constant and the outer diameter of the vibrating needle changes along the length thereof;

DESCRIPTION OF ILLUSTRATED EMBODIMENTS

Figure 1:
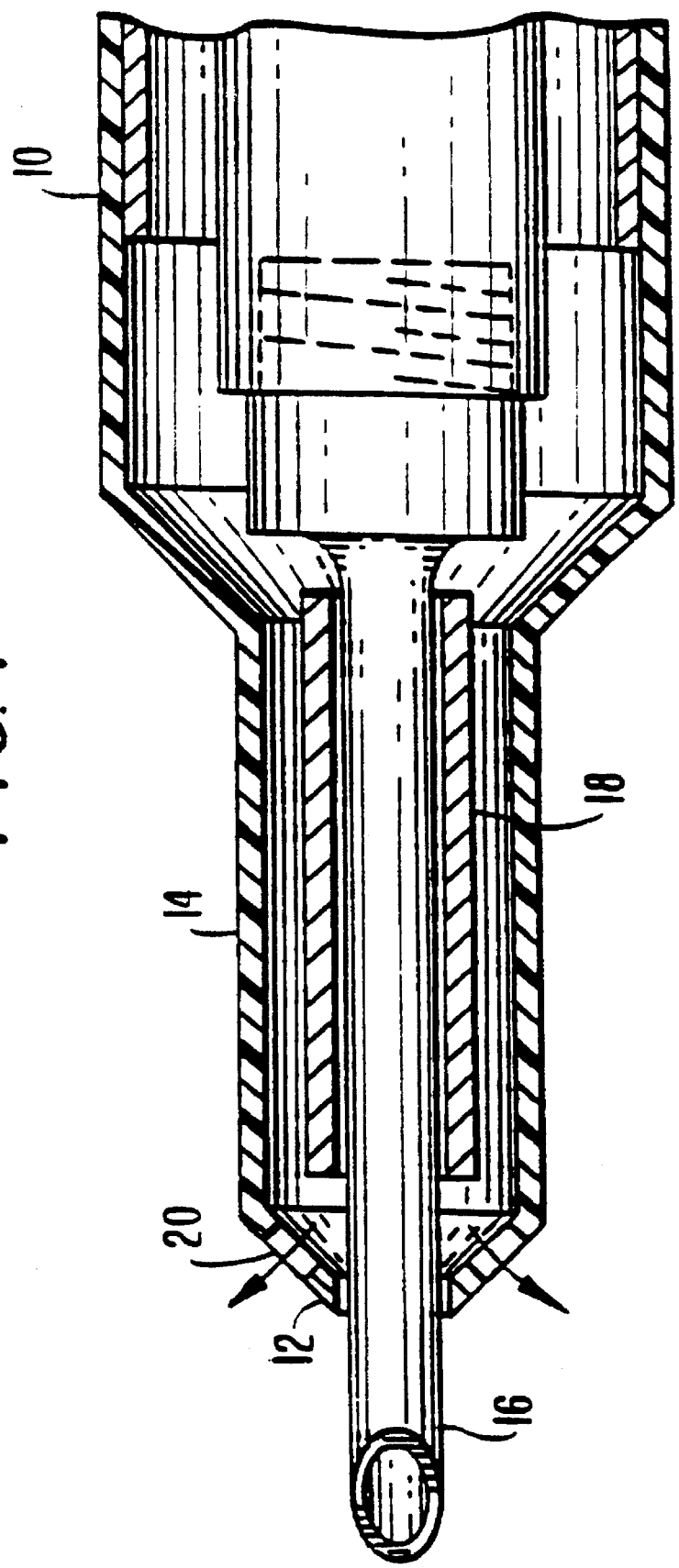
FIG. 1 depicts a cross sectional view of a phacoemulsification instrument modified in accordance with the invention.
Figure 1A:
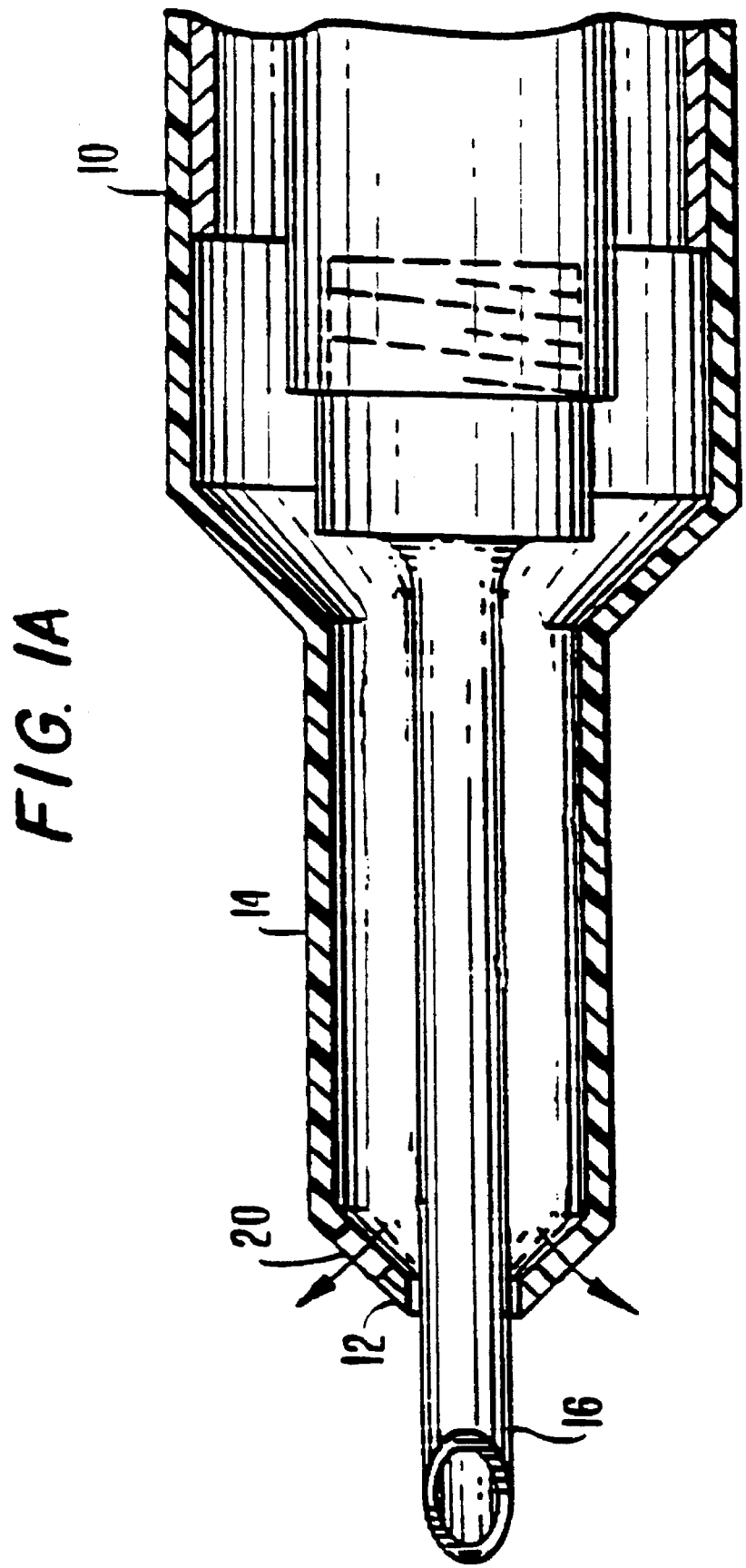
FIG. 1A depicts a cross sectional view of an alternative phacoemulsification instrument, and shows that the preferred interior sleeve 18 (shown in other FIGS.) is not required to fall within the scope of the present invention.

FIGS. 1-8 are cross-sectional views of a phacoemulsification instrument including a hollow, compressible infusion sleeve 10 having a tapered, ported, distal end portion 12 and a cylindrical portion 14. The instrument also includes a hollow vibrating needle 16, a rigid, hollow sleeve 18, and discharge ports 20.

Figure 9:
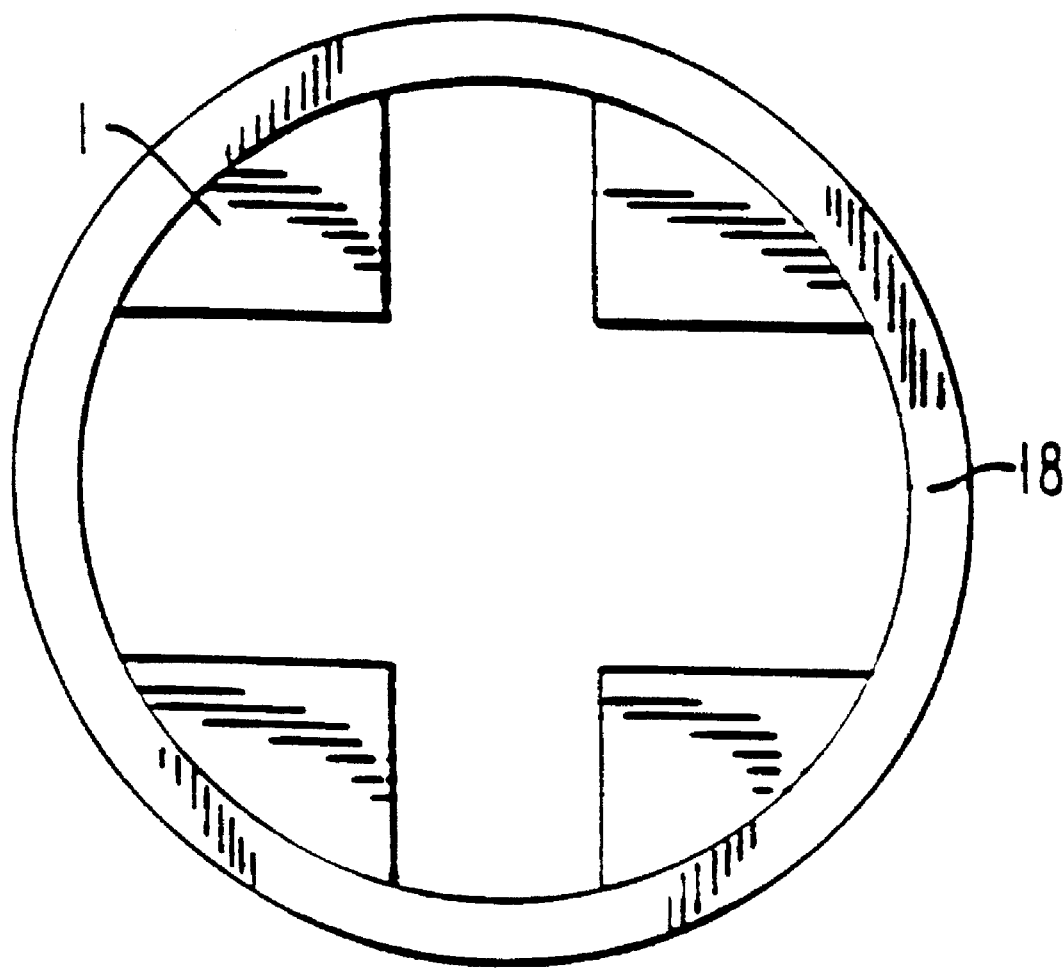
FIG. 9 depicts an embodiment of a rigid hollow sleeve in accordance with the invention for a phacoemulsification instrument.

FIG. 9 is a side view of a rigid, hollow sleeve 18 of a phacoemulsification instrument including spacers 1.

In accordance with known principles of operation employed in phacoemulsification devices, the hollow needle 16 is caused to vibrate at ultrasonic frequencies, causing disintegration of tissue proximate to the tip of needle 16. A saline solution is utilized as a cooling and irrigation fluid, and is introduced at a proximal end of the device and exits through ports 20 located at the tapered, ported distal end 12. Operation of a device of this general nature is described in the previously-incorporated Mackool patents.

In conventional phacoemulsification devices utilizing a flexible infusion sleeve, the flexible infusion sleeve can collapse around the vibrating needle, causing heat build-up due to friction between the sleeve and the needle. The invention obviates this problem by utilizing inner sleeve 18, and/or by specifically adapting the flexible infusion sleeve and/or outer needle surfaces to reduce the friction therebetween, as described below under the heading DESCRIPTION OF THE IMPROVEMENT.

FIG. 2 depicts an embodiment of the invention in which the outer deformable sleeve 10 closely conforms to the vibrating needle at the tapered distal end 12. The close fit between the outer deformable sleeve 10 and the vibrating needle limits distal migration of the rigid, hollow sleeve 18.

FIG. 3 depicts an embodiment of the invention in which the vibrating needle 16 has protuberances 24 at selected points around the periphery thereof. These protuberances 24 limit distal migration of the rigid, hollow sleeve 18.

FIG. 4 depicts an embodiment of the invention wherein the vibrating needle 16 has an inward taper which defines a proximal portion and a distal portion of the needle. The distal portion has a relatively large inner diameter I1—I1 and outer diameter O1—O1. The proximal portion has a smaller inner diameter and outer diameter. As illustrated in FIG. 4, this difference in diameter limits distal migration of the rigid, hollow sleeve 18, since the outer diameter of the distal portion of the needle is larger than the inner diameter of sleeve 18. In the illustrated embodiment, the wall thickness of the needle is substantially constant.

FIG. 5 depicts an embodiment of the invention having a tapered vibrating needle with a distal portion and a proximal portion. The outer diameter of the proximal portion is smaller than the outer diameter of the distal portion, while the inner diameter of the needle remains constant along the length of the needle. Thus, the wall thickness of the proximal portion is reduced. This geometry limits distal migration of sleeve 18, since the outer diameter of the distal portion of the needle is larger than the inner diameter of sleeve 18.

Figure 6:
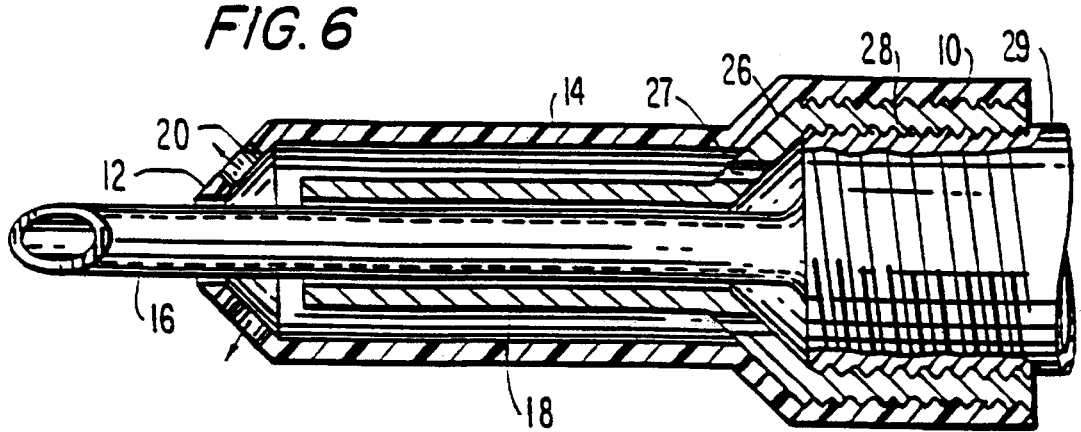
FIG. 6 depicts a fifth embodiment of a phacoemulsification instrument in accordance with the invention; including details of a rigid, hollow sleeve, wherein the rigid hollow sleeve has a ported proximal expansion portion and a threaded extension.

FIG. 6 depicts an embodiment of the invention wherein the rigid hollow sleeve 18 has a ported proximal expansion portion 26 and a threaded extension 28 which is externally and internally threaded. The threaded extension 28 screwably attaches to the needle support 29 which axially oscillates the needle with the threaded extension 28 preventing distal migration of the rigid, hollow sleeve 18. The ports 27 allow saline solution to flow around the rigid, hollow sleeve 18. The figure further shows that the hollow compressible infusion sleeve 10 is screwably attached to external threads of the rigid, hollow sleeve threaded extension.

Figure 7:
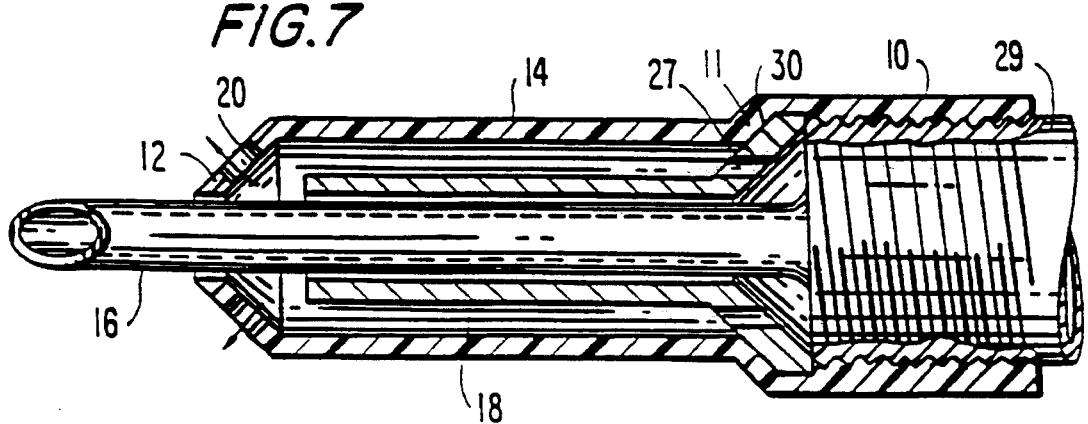
FIG. 7 depicts a sixth embodiment of a phacoemulsification instrument in accordance with the invention; including details of a rigid, hollow sleeve, wherein the rigid hollow sleeve has a ported proximal flange portion.

FIG. 7 depicts an embodiment of the invention wherein the rigid hollow sleeve 18 has a ported proximal flange portion 30. The ported proximal expansion end portion 30 limits distal migration of the rigid hollow sleeve 18 by abutting against an internal shoulder 11 of the hollow compressible infusion sleeve 10. Again, the ports 27 allow saline solution to flow around the rigid, hollow sleeve 18 internal threads on the hollow compressible infusion sleeve 10 mate with external threads needle support 29.

Figure 8:
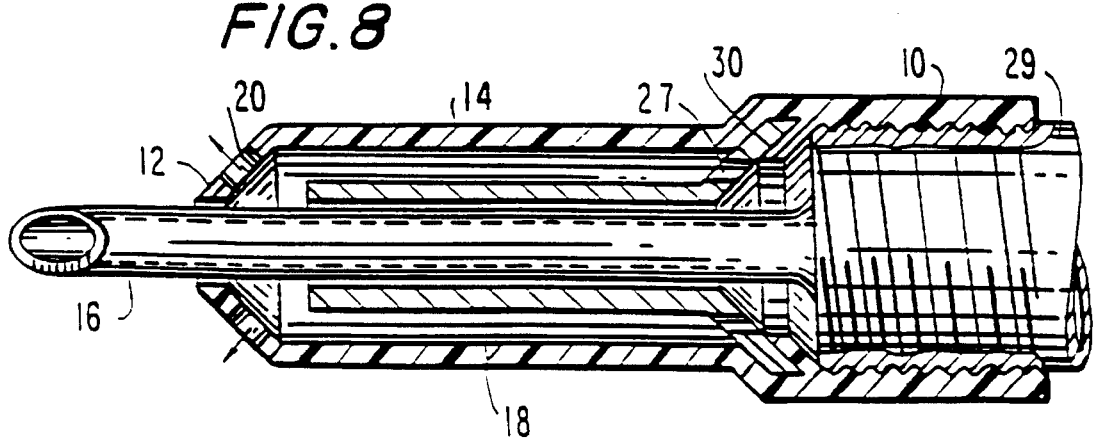
FIG. 8 depicts a seventh embodiment of a phacoemulsification instrument in accordance with the invention; including details of a rigid, hollow sleeve, wherein the rigid hollow sleeve has a ported proximal flange portion coupled to the deformable sleeve.

FIG. 8 depicts an embodiment of the invention wherein the rigid hollow sleeve 18 has a ported proximal flange portion 30. The ported proximal flange portion 30 is received in an annular slot in the hollow compressible infusion sleeve 10 and prevents distal migration of the rigid hollow sleeve 18.

FIG. 9 depicts a side view of a rigid, hollow sleeve 18 of a phacoemulsification instrument wherein the rigid, hollow sleeve 18 includes spacers 1 which can be located at each end of the sleeve or its spaced locations along the inner diameter thereof. The spacers 1 prevent large surface contact between the hollow, vibrating needle 16 and the rigid, hollow sleeve 18, while still allowing the maximum amount of fluid to circulate between the rigid, hollow sleeve 18 and the hollow, vibrating needle 16. As will be obvious to one skilled in the art, there is still no need for absolute concentricity, and only a minimal amount of surface area of the rigid, hollow sleeve 18 will come into contact with the hollow, vibrating needle 16.

In the embodiment shown in FIGS. 1–8 the hollow, compressible infusion sleeve 10 may be constructed of silicone or other compressible materials. The rigid, hollow sleeve 18 may be formed of a rigid plastic or other suitable material. Further, discharge ports 20 are angled for radial discharge of fluid thus avoiding the direction of fluid parallel to the needle 16, which would oppose the fractured cataract being drawn into the interior of the hollow vibrating needle 16.

In the embodiment of the invention shown in FIG. 2, as well as in the other embodiments shown, it is noteworthy that the tapered, ported, distal end 12 of the silicone infusion sleeve 10 will not be compressed against the vibrating needle 16 since this portion of the instrument is never maintained within the incision during periods of vibration of the needle 16.

DESCRIPTION OF THE IMPROVEMENT

In accordance with the invention, it is desirable to reduce mechanical coupling between the surfaces of the sleeve(s), the tissue surrounding the outer sleeve, the rigid inner sleeve (if one exists), and needle shaft by minimizing the frictional force created by the needle motion. Since the movements of the needle include high and/or low frequency motion, it may be necessary to minimize the frictional force for both high and low frequency motions. Minimizing the frictional force created by the frictional contact of the surface(s) can substantially reduce undesirable heat generation.

It is possible to estimate the maximum frictional force which can be permitted without causing undesirable thermally-induced tissue damage. The normal temperature of body tissues is 37° C. The surface tissue of the eye is normally slightly cooler, typically 35° C. It is also known that temperatures of 55° C. or greater can cause damage to ocular tissue. Therefore, it is necessary to design the needle/sleeve, sleeve/sleeve, and/or sleeve/tissue interface so that the temperature rise of ocular tissue does not exceed 19° C., which would lead to a tissue temperature of 54° C. Heat imparted to ocular tissue during ultrasonic surgery is generally either removed by local blood flow, by fluid which circulates within and/or around the sleeve and needle shaft as well as within the anterior chamber of the eye, and/or by irrigating fluid which may be used to bathe the outer surface of the eye in order to keep it moist and cool. It is known that the rate of fluid flow during the phacoemulsification procedure is highly variable. At certain times, for example during periods of complete obstruction of the ultrasonic needle by aspirated tissue, the rate of fluid flow through the eye, ultrasonic needle and infusion sleeve may be essentially zero.

In a worst-case scenario of an ultrasonic transducer, driver and needle with a mass of 23 grams, a frequency of 60 KHz and a stroke length of 0.004 inches, the following calculation can be made. Ultrasonic power is approximately 32 Joules/second. If 80% of this energy is dissipated on the sleeve(s), the heat energy released would be 6 calories/second. Assuming that the area of a sleeve in contact with the tissue is 15–20 square millimeters and that a 3 mm thick region of tissue surrounding the sleeve accepts all the heat, temperature rise (in this region of tissue) would be 10°–14° C./second. Within this region of tissue and fluids, there will exist a temperature gradient, with the tissue in direct contact with the sleeve having the highest temperatures, and that most separated from direct sleeve contact experiencing lesser temperature elevations.

Under these circumstances, the 55° C. limit would be reached in 1.5–2.0 seconds of full-power application by the ultrasonic transducer. In accordance with the invention, a dynamic friction coefficient of 0.1 between the outer needle surface and the inner sleeve surface will reduce heat generation by 90%, and will allow at least 15–20 seconds of operation before a tissue temperature of 55° C. is reached. Accordingly, one or both of these surfaces, and/or all other sleeve surfaces, should be made slippery and relatively non-compliant, in order to avoid mechanical coupling throughout the frequency spectrum, which ranges from 0.1 to 60,000 Hz. Moreover, these opposing surfaces should preferably have a dynamic friction coefficient of between about 0.05 and 0.25, and most preferably less than about 0.15. Also, as depicted in FIG. 1 A, in accordance with the present invention, by suitably coating the outer surface of the needle and the inner and/or outer surface of the infusion sleeve, it is possible to reduce friction to such an extent that it is not necessary to use a separate rigid infusion sleeve between the needle and the outer sleeve.

PREFERRED SURFACE TREATMENT TECHNIQUES

For optimal functioning, the compressible sleeve which is in contact with the surrounding tissue should preferably be compliant to the forces exerted on it by such tissue, so that it can develop good contact with the entire surface of the incision, and it should have a hard (non-compliant) inner surface which will prevent development of a mechanical interlock or binding with the outer surface of the shaft (or the outer surface of the rigid sleeve, when such sleeve is present), even when pressure from the ocular tissue deforms the sleeve, causing it to press against either of these surfaces. Therefore, both the inner and outer surfaces of the sleeve should be sufficiently hydrophilic so that the contact angle of water on these surfaces is 0–30 degrees, and preferably less than 25 degrees. Additionally, while both surfaces may have hard (non-compliant) surfaces, a design comprising a hard inner sleeve surface and a compliant outer sleeve surface is preferred, as this will more readily permit the sleeve to deform to the shape of the incision through which it is inserted. There are several ways by which such a sleeve can be fabricated.

As an example, the sleeve can be made of an elastomeric material, such as poly (polyoxymethylene-400 diacrylate), with a hard coating applied to the inner and/or outer surface. The hard coating may be applied by dip-coating or spray-coating the surface with a mixture of highly functional acrylates and methacrylates incorporating a photoinitiator, such as a mixture of pentaerythritol tetraacrylate, highly alkoxylated aliphatic diacrylates, and a polymerizable benzophenone or acetophenone derivative, such as Durcure 1173, available from Ciba Geigy Corp. Traditionally, the concentration of tetraacrylate will be between 3 and 15%, preferably 5–7%, the concentration of the photoinitiator will be between 0.2 and 8%, preferably 0.5–2%, and the rest will be diacrylate. The resin layer is applied to the surface(s) of the sleeve, then cured in situ by application of ultraviolet radiation. Similarly, formulations which can be cured by application of heat may also be used.

Alternatively (or additionally), the surface(s) may be made hydrophilic, so that the surface(s) have a low contact angle with water. An example of a resin formulation which would produce a hard, hydrophilic surface layer would be poly(oxymethylene)-400 diacrylate at a level of 70–90%, preferably 75–85%, vinyl formamide at a level of 5–15%, preferably 7–10%, pentaerethrytol tetraacrylate at the level of 3–15%, preferably 5–7%, and a photoinitiator, such as Durcure 1173 at the level of 0.2–8%, preferably 2–5%. This formulation may also be readily modified to be heat curable.

In all cases, the hard surface layer is strongly bonded to the sleeve by developing an interpenetrating network, so that the composition of the sleeve material develops a gradient, going from a cross-linked network with compliant, elastomeric properties to a network of higher cross-link density which is glassy and non-compliant at use temperatures (i.e. 20°–60° C.).

It is also possible to apply an inorganic coating to the surface(s). For example, a coating of $SiO_x$ or $Al_2O_3$ may be applied using an electron beam deposition method. Such coating facilities are commercially available.

The following examples illustrate applications of the present invention, whereby increased hydrophilicity of the outer surface of the needle shaft and the inner and outer surfaces of the sleeve are obtained. All surfaces are relatively non-compliant, as preferred to advantageously reduce friction.

EXAMPLE 1

The needle shaft is composed of a metallic or composite structure. The shaft is coated with a hydrophilic coating of poly (n-vinyl pyrrolidone). The coating is about 100 microns thick, and is applied by plasma polymerization of vinyl pyrrolidone directly on the surface of the needle shaft. The sleeve is made of a cross-linked acrylic thermoset layer (such as a copolymer of an aliphatic di- or tri- acrylate and a monomer which creates a high glass transition polymer, such as cyclohexyl methacrylate), or a hard polyurethane resin, containing hard segments of an aromatic urethane on the inner surface, which may be rendered hydrophilic, with the bulk comprising an elastomeric acrylate polymer, such as an aliphatic mono- or di-acrylate, e.g., poly (propyl acrylate-co-hydroxyethyl methacrylate).

EXAMPLE 2

The needle shaft is metallic, and the sleeve is made of an inner layer of hard, cross-linked, glassy, tough thermoset resin, which is preferably rendered hydrophilic, with an outer and inner coating of an elastomeric, hydrophilic copolymer of hydroxyethyl methacrylate and polyethylene glycol (400) diacrylate. The outer coating is about 0.25 mm thick, while the inner coating is about 100 microns in thickness. The coatings may be applied to the sleeve by either a dip coating process, or by in-situ polymerization of a thin layer of the appropriate monomer formulation.

It will thus be seen that the invention efficiently attains the objects set forth above, among those made apparent from the preceding description. In particular, the invention provides a relatively inexpensive, improved apparatus for performing cataract surgery.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A surgical instrument for removing tissue through an incision in a patient comprising:

an infusion sleeve that is compressible and hollow to define a lumen, said infusion sleeve having a tapered, ported, distal end portion and a cylindrical portion; said cylindrical portion extending from said tapered, ported, distal end portion;

a needle within said lumen and arranged to define a space between said sleeve and said needle, said needle being hollow and vibratable;

a rigid sleeve that is hollow and surrounding a portion of said needle and being rigid in construction;

said rigid sleeve having an inner diameter that is larger than an outer diameter of said needle, thereby defining a path for fluid flow between said needle and said infusion sleeve, said rigid sleeve being interposed radially between said infusion sleeve and said needle to block said infusion sleeve from collapsing onto said needle when said infusion sleeve compresses;

an inhibitor for inhibiting a distal migration of said rigid sleeve away from said infusion sleeve; and wherein said needle and said tapered, ported distal end portion of said infusion sleeve each have a surface that interfaces each other to create friction in response to rubbing contact between said surfaces caused by vibrating motion of said needle so as to generate a temperature rise in surrounding body tissue, at least one of the surfaces of said needle and infusion sleeve being formed to keep said temperature rise below that which would raise a temperature of said body tissues from 37° C. to 55° C. due to said rubbing contact for longer than 2 seconds.

2. A surgical instrument corresponding to claim 1 wherein said needle is constructed from carbon metallic matrix composite.

3. A surgical instrument corresponding to claim 1 wherein said needle is constructed from carbon organic matrix composite.

4. A surgical instrument for removing tissue through an incision in a patient according to claim 1, wherein said inhibitor includes:

a ported proximal flange portion intersecting and extending outward from said rigid sleeve;

a threaded extension, said threaded extension intersecting with and extending away from said ported proximal flange portion;

said threaded extension being screwably engageable with said hollow, vibrating needle, needle support.

5. A surgical instrument for removing tissue through an incision in a patient according to claim 1, wherein said inhibitor includes a ported proximal flange portion intersecting and extending outward from said rigid sleeve to limit migration of said rigid sleeve towards said tapered ported distal end.

6. A surgical instrument for removing tissue through an incision in a patient according to claim 1, wherein:

said infusion sleeve contains a slot for receiving said rigid hollow sleeve; and said rigid, sleeve is coupled to said infusion sleeve.

7. A surgical instrument for removing tissue through an incision in a patient according to claim 1, wherein said rigid, sleeve further comprises spacers attached to said rigid sleeve, said spacers extending inward towards a longitudinal axis of said rigid sleeve.

8. A surgical instrument for removing tissue through an incision in a patient according to claim 1, wherein one or more of said sleeve surface(s) has/have a surface energy close to that of water, such that the contact angle of water on said surface is between 0 and 30 degrees.

9. A surgical instrument for removing tissue through an incision in a patient according to claim 1, wherein said outer needle surface has a surface energy close to that of water, such that the contact angle of water on said surface is between 0 and 30 degrees.

10. A surgical instrument for removing tissue through an incision in a patient according to claim 1, wherein said outer needle surface is coated with a bio-compatible lubricant.

11. A surgical instrument for removing tissue through an incision in a patient according to claim 10, wherein said bio-compatible lubricant is graphite.

12. A surgical instrument for removing tissue through an incision in a patient according to claim 1, wherein said bio-compatible lubricant is molybdenum sulfide.

13. A surgical method for removing tissue through an incision in a patient comprising the steps of:

inserting a deformable hollow sleeve into said incision;

vibrating a hollow needle through said sleeve;

supplying fluid through said hollow sleeve that is exterior of said needle into said patient; and withdrawing the fluid through the hollow of said needle; the stem of vibrating the hollow needle including generating friction from rubbing contact at an interface such that a temperature of surrounding body tissues at 37° C. before the rubbing contact arises increases at most to a temperature that is less than 55° C. throughout an entire duration of said rubbing contact for longer than 2 seconds, said interface being located between any of the outer surface of the vibrating needle and neighboring inner surface of the hollow sleeve, and the outer surface of said sleeve and the incision.

14. A surgical method as defined in claim 13, further comprising maintaining the surface energy of at least one surface of the hollow sleeve and an outer surface of the vibrating needle close to that of water such that a contact angle of water on said at least one surface and said outer surface is between 0 and 30 degrees.

15. A surgical method as defined in claim 13, further comprising coating the outer surface of the vibrating needle with a bio-compatible lubricant.

16. A surgical method for removing tissue through an incision in a patient as defined in claim 15, wherein said bio-compatible lubricant is graphite.

17. A surgical method for removing tissue through an incision in a patient as defined in claim 15, wherein said bio-compatible lubricant is molybdenum sulfide.

18. A surgical method as defined in claim 13, further comprising maintaining the surface energy of the inner surface of the hollow sleeve close to that of water so that a contact angle of water on said surface is between 0 and 30 degrees, and coating the outer surface of the vibrating needle with a bio-compatible lubricant.

19. A surgical instrument for removing tissue through an incision in a patient comprising:

a hollow infusion sleeve having a contacting surface;

a hollow needle that is vibratable, said hollow needle protruding through said infusion sleeve, said needle having a contacting surface;

at least one of said contacting surfaces being sufficiently hydrophillic so as to have a surface energy close to that of water so that a contact angle of water on said one contacting surface is between 0 and 30 degrees.

20. A component for use in ultrasonic surgery comprising a hollow tube formed from a compliant material;

at least one coating layer formed on at least one surface of said tube, said layer being free from being compliant in contrast to that of said tube; and an interpenetrating network bonding said tube and said layer together, said network including a composition that includes a first region with a cross-linked network with compliant, elastomeric properties and a second region with a network of higher cross-link density that is glassy and free from being compliant at temperatures between 20° and 60° C.

21. A component as defined in claim 20, wherein said hollow tube has an inner surface coated with a layer that is free from being compliant. sulfide.

22. A component as defined in claim 21, wherein said inner surface has a surface energy close to that of water, so that the contact angle of water on said surface is between 0 and 30 degrees.

23. A component as defined in claim 20, wherein said hollow tube has an outer surface with a surface energy close to that of water, so that the contact angle of water on said outer surface is between 0 and 30 degrees.

24. A surgical instrument for removing tissue through an incision in a patient comprising:

a hollow infusion sleeve;

a hollow, vibrating needle, having an inner needle surface, located at an inner needle diameter, and an outer needle surface, located at an outer needle diameter;

said hollow, vibrating, needle protruding through said infusion sleeve and extending into the patient's body during the removal of tissue;

a contacting portion of the surface of said sleeve contacting said needle during the removal of tissue; and said needle being formed of a composite material having a higher strength-to-weight ratio as compared to titanium.

25. A surgical instrument for removing tissue through an incision in a patient comprising:

a hollow, compressible infusion sleeve;

said hollow, compressible infusion sleeve having a tapered, ported, distal end portion and having an extreme end portion;

said hollow, compressible infusion sleeve further including a cylindrical portion;

said cylindrical portion intersecting with and extending away from said tapered, ported, distal end portion;

a hollow, vibrating needle, having an inner needle surface, located at an inner needle diameter, and an outer needle surface, located at an outer needle diameter;

a needle support;

said hollow, vibrating, needle extending into a patient during the removal of tissue;

said cylindrical portion and said tapered, ported, distal end portion surrounding said hollow, vibrating needle with there being a space between the extreme end portion of said tapered, ported distal end portion and the hollow, vibrating needle;

a rigid, hollow, sleeve surrounding a portion of said hollow, vibrating needle;

said sleeve having an outer sleeve surface, located at an outer sleeve diameter, and an inner sleeve surface, located at an inner sleeve diameter;

said inner sleeve diameter being larger than said outer needle diameter, thereby defining a path of fluid between said hollow vibrating needle and said rigid, hollow, sleeve;

said rigid, hollow, sleeve being surrounded by said cylindrical portion whereby said rigid, hollow, sleeve prevents the hollow, compressible infusion sleeve from collapsing against said hollow, vibrating needle;

an inhibitor for inhibiting the distal migration of said rigid, hollow, sleeve; and said needle being formed of a composite material having a higher strength-to-weight ratio as compared to titanium.

* * * * *